(12) United States Patent
Kitao et al.

(10) Patent No.: US 9,249,256 B2
(45) Date of Patent: Feb. 2, 2016

(54) TRIEPOXY COMPOUND AND METHOD FOR PRODUCING SAME

(75) Inventors: Kyuhei Kitao, Himeji (JP); Hideyuki Takai, Himeji (JP); Michihiro Sugahara, Himeji (JP)

(73) Assignee: DAICEL CORPORATION, Osaka-shi (JP)

( * ) Notice: Subject to any disclaimer, the term of this patent is extended or adjusted under 35 U.S.C. 154(b) by 138 days.

(21) Appl. No.: 14/344,698

(22) PCT Filed: Sep. 4, 2012

(86) PCT No.: PCT/JP2012/072422
§ 371 (c)(1),
(2), (4) Date: Mar. 13, 2014

(87) PCT Pub. No.: WO2013/038945
PCT Pub. Date: Mar. 21, 2013

(65) Prior Publication Data
US 2014/0357836 A1    Dec. 4, 2014

(30) Foreign Application Priority Data

Sep. 14, 2011  (JP) ................................ 2011-200251

(51) Int. Cl.
| | | |
|---|---|---|
| C08G 59/32 | (2006.01) | |
| C08G 59/34 | (2006.01) | |
| C07D 301/14 | (2006.01) | |
| C07D 303/12 | (2006.01) | |
| C08G 59/02 | (2006.01) | |
| C07D 303/04 | (2006.01) | |
| C08L 63/00 | (2006.01) | |
| C07C 2/76 | (2006.01) | |
| C07C 6/04 | (2006.01) | |

(52) U.S. Cl.
CPC .............. *C08G 59/3218* (2013.01); *C07C 2/76* (2013.01); *C07C 6/04* (2013.01); *C07D 301/14* (2013.01); *C07D 303/04* (2013.01); *C07D 303/12* (2013.01); *C08G 59/02* (2013.01); *C08L 63/00* (2013.01); *C07C 2101/16* (2013.01)

(58) Field of Classification Search
CPC .... C08L 63/00; C08G 59/27; C08G 59/3218; C08G 59/32
USPC ............................ 549/547, 512, 525; 528/418
See application file for complete search history.

(56) References Cited

U.S. PATENT DOCUMENTS

| | | | |
|---|---|---|---|
| 3,255,214 A | | 6/1966 | Phillips et al. |
| 3,565,922 A | * | 2/1971 | Rudy et al. ............... C06B 45/10 549/546 |
| 6,245,828 B1 | | 6/2001 | Weinmann et al. |
| 2002/0002212 A1 | | 1/2002 | Weinmann et al. |
| 2004/0024113 A1 | | 2/2004 | Weinmann et al. |
| 2004/0167315 A1 | | 8/2004 | Sasa |
| 2006/0194933 A1 | | 8/2006 | Takai et al. |
| 2006/0264529 A1 | | 11/2006 | Sasa |

(Continued)

FOREIGN PATENT DOCUMENTS

| | | |
|---|---|---|
| GB | 2 400 849 A | 10/2004 |
| JP | 63-264625 A | 11/1988 |

(Continued)

OTHER PUBLICATIONS

International Search Report Issued in PCT/JP2012/072422, mailed on Nov. 20, 2012.

(Continued)

*Primary Examiner* — Megan McCulley
(74) *Attorney, Agent, or Firm* — Birch, Stewart, Kolasch & Birch, LLP

(57) ABSTRACT

Provided are: a novel triepoxy compound capable of forming, through polymerization, a cured article having excellent heat resistance; a production method thereof; a curable composition including the triepoxy compound; and a cured article obtained by curing the curable composition.

The triepoxy compound according to the present invention is represented by Formula (1). The triepoxy compound represented by Formula (1) may be obtained typically by oxidizing a compound represented by Formula (2) with an oxidizing agent. In Formulae (1) and (2), $R^1$ to $R^{20}$ are the same as or different from one another and each represent hydrogen atom, methyl group, or ethyl group. Formulae (1) and (2) are expressed as follows:

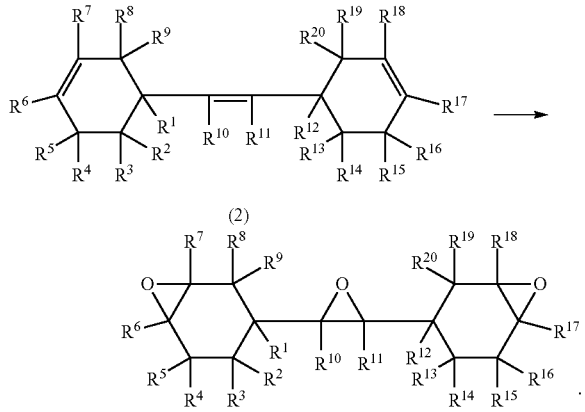

7 Claims, No Drawings

(56) References Cited

U.S. PATENT DOCUMENTS

2007/0179256 A1 8/2007 Kitao et al.
2009/0041945 A1* 2/2009 Ookubo ............... B41M 5/0023
 427/511

FOREIGN PATENT DOCUMENTS

| JP | 2005-68303 A | 3/2005 |
| JP | 2005-263811 A1 | 9/2005 |
| JP | 2006-52187 A | 2/2006 |
| JP | 2007-146021 A | 6/2007 |
| WO | WO 98/22521 A1 | 5/1998 |
| WO | WO 2005/090325 A1 | 9/2005 |
| WO | WO 2015080159 A1 * | 6/2015 ............. C08G 59/20 |

OTHER PUBLICATIONS

Kakuchi et al. "Ring-opening and ring-forming polymerization of 1, 2:5, 6:9, 10-triepoxydecane leading to a highly regioselective polymer consisting of octahydrobifuranyl unit," Macromolecules, 2000, vol. 33, No. 2, pp. 246-247.

The Japan Society of Epoxy Resin Techonology, Sosetsu Epoxy Jushi Kisohen I, Nov. 19, 2003, p. 301.

* cited by examiner

TRIEPOXY COMPOUND AND METHOD FOR PRODUCING SAME

TECHNICAL FIELD

The present invention relates to a triepoxy compound and a production method thereof, which triepoxy compound can be rapidly cured by polymerization to form a cured article having excellent heat resistance.

BACKGROUND ART

Epoxy compounds are known to give cured articles excelling in properties such as electric properties, moisture vapor resistance, heat resistance, and toughness. The epoxy compounds are used typically in machine part materials, electric/electronic component materials, automotive part materials, civil engineering and construction materials (building materials), molding materials, coating materials, adhesives, and sealants.

The field of electric/electronic component materials recently moves towards higher-density packaging of electronic components onto printed circuit boards. The field employs, as a main stream, a surface mounting technique in which a semiconductor package is directly soldered to a printed circuit board surface. In the surface mounting technique, the semiconductor package is directly exposed to an elevated temperature upon reflow soldering, and this requires epoxy compounds capable of forming cured articles being resistant to reflow heat. The field more and more employs lead-free solders from the viewpoint of environmental protection. Reflow soldering using such lead-free solders is performed at a reflow temperature higher than those in customary techniques, because the lead-free solders have preset melting points higher than those of customary solders. Under these present circumstances, demands have been made to provide an epoxy compound that gives a cured article having such reflow-heat resistance as to resist deformation and cracking caused by heat even when employed in the lead-free solder mounting.

Epoxy compounds are exemplified by compounds having at least one glycidyl group in molecule; and compounds having at least one alicyclic epoxy group in molecule. The compounds having at least one alicyclic epoxy group in molecule are known to give cured articles having heat resistance superior to that of cured articles of the compounds having at least one glycidyl group in molecule. Known compounds having at least one alicyclic epoxy group in molecule are exemplified by compounds having two alicyclic epoxy groups per molecule (e.g., Patent Literature (PTL) 1 and PTL 2). With employment of the lead-free solder mounting, demands have been made to provide an epoxy compound capable of forming a cured article having further excellent heat resistance and being applicable to the lead-free solder mounting.

CITATION LIST

Patent Literature

PTL 1: Japanese Unexamined Patent Application Publication (JP-A) No. S63-264625
PTL 2: JP-A No. 2007-146021

SUMMARY OF INVENTION

Technical Problem

Accordingly, an object of the present invention is to provide a novel triepoxy compound and a production method thereof, which triepoxy compound, when polymerized, can give a cured article having excellent heat resistance.

Another object of the present invention is to provide a curable composition including the novel triepoxy compound; and a cured article which is obtained by curing the curable composition and has excellent heat resistance.

Solution to Problem

After intensive investigations to achieve the objects, the present inventors have found that a novel triepoxy compound including two epoxycyclohexane rings combined through ethylene oxide can be obtained by oxidizing a compound corresponding to ethylene, except for substituting two hydrogen atoms each with a cyclohexenyl group; and that the novel triepoxy compound has two alicyclic epoxy groups and one non-alicyclic epoxy group, has crosslinking points in a large number per monomeric unit, and, when polymerized, can give a cured article having a densely three-dimensionally crosslinked structure and having excellent heat resistance and toughness. The present invention has been made based on these findings. As used herein the term "alicyclic epoxy group" refers to a group including a three-membered ring composed of one oxygen atom and two adjacent carbon atoms constituting an alicycle; and the term "non-alicyclic epoxy group" refers to a group including a three-membered ring composed of one oxygen atom and two adjacent carbon atoms (excluding carbon atoms constituting an alicycle).

Specifically, the present invention provides a triepoxy compound represented by Formula (1) expressed as follows:

[Chem. 1]

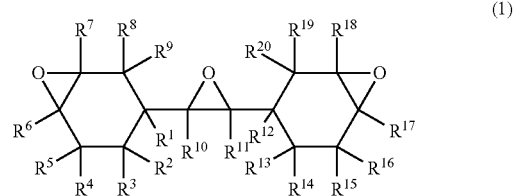

where $R^1$, $R^2$, $R^3$, $R^4$, $R^5$, $R^6$, $R^7$, $R^8$, $R^9$, $R^{11}$, $R^{12}$, $R^{13}$, $R^{14}$, $R^{15}$, $R^{16}$, $R^{17}$, $R^{18}$, $R^{19}$, and $R^{20}$ are the same as or different from one another and each represent hydrogen atom, methyl group, or ethyl group.

The present invention further provides a method for producing a triepoxy compound. The method includes the step of oxidizing a compound represented by Formula (2) with an oxidizing agent to give a triepoxy compound represented by Formula (1),
Formula (2) expressed as follows:

[Chem. 2]

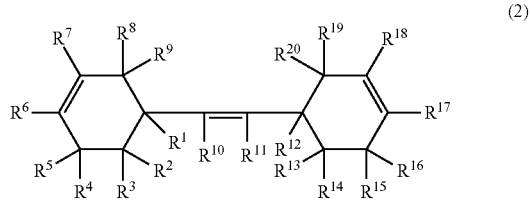

where $R^1$ to $R^{20}$ are the same as or different from one another and each represent hydrogen atom, methyl group, or ethyl group; and Formula (1) expressed as follows:

[Chem. 3]

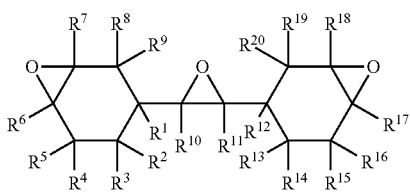

(1)

where $R^1$ to $R^{20}$ are as defined above.

The oxidizing agent is preferably a peracid.

The method for producing a triepoxy compound preferably includes the steps of: subjecting a compound represented by Formula (3) and a compound represented by Formula (3') to a metathesis reaction in the presence of a catalyst to give a compound represented by Formula (2); and oxidizing the prepared compound represented by Formula (2) with the oxidizing agent, wherein Formula (3) is expressed as follows:

[Chem. 4]

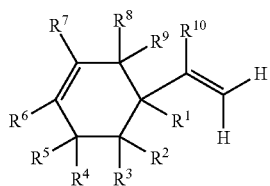

(3)

where $R^1$ to $R^{10}$ are the same as or different from one another and each represent hydrogen atom, methyl group, or ethyl group;

Formula (3') is expressed as follows:

[Chem. 5]

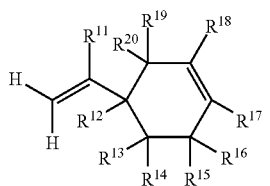

(3')

where $R^{11}$ to $R^{20}$ are the same as or different from one another and each represent hydrogen atom, methyl group, or ethyl group; and Formula (2) is expressed as follows:

[Chem. 6]

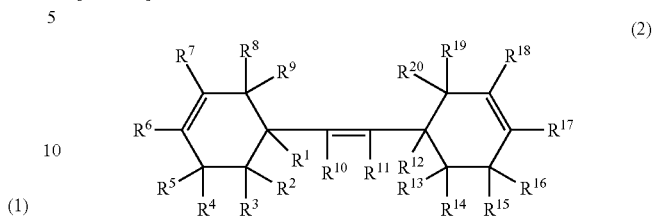

(2)

where $R^1$ to $R^{20}$ are as defined above.

The catalyst is preferably a ruthenium complex catalyst or a cobalt--molybdenum catalyst.

The present invention further provides a curable composition including a triepoxy compound represented by Formula (1) expressed as follows:

[Chem. 7]

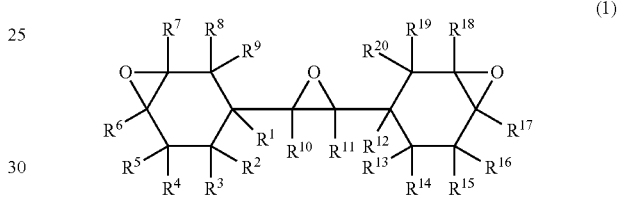

(1)

where $R^1$ to $R^{20}$ are the same as or different from one another and each represent hydrogen atom, methyl group, or ethyl group.

In addition and advantageously, the present invention provides a cured article obtained by curing the curable composition.

Advantageous Effects of Invention

The novel triepoxy compound represented by Formula (1) according to the present invention has two alicyclic epoxy groups and one non-alicyclic epoxy group per one molecule (namely, has crosslinking points in a large number) and, when polymerized, can form a cured article that has a high crosslinking density and exhibits extremely excellent heat resistance and toughness. The novel triepoxy compound represented by Formula (1) according to the present invention is useful particularly in the fields typically of machine part materials, electric/electronic component materials, automotive part materials, civil engineering and construction materials (building materials), molding materials, coating materials, fiber reinforced plastics (FRPs; such as glass fiber reinforced plastics (GFRPs) and carbon fiber reinforced plastics (CFRPs)) materials, and plastic forming materials.

DESCRIPTION OF EMBODIMENTS

Triepoxy Compound

A triepoxy compound according to an embodiment of the present invention is represented by Formula (1). In Formula (1), $R^1$ to $R^{20}$ are the same as or different from one another and each represent hydrogen atom, methyl group, or ethyl group. The groups $R^1$ to $R^{20}$ are independent groups; and it does not occur that two or more groups selected from the group consisting of $R^1$ to $R^{20}$ are combined to form a ring with carbon atoms constituting the alicycle(s).

Of triepoxy compounds according to the present invention, preferred are triepoxy compounds represented by Formula (1) in which $R^1$ to $R^{20}$ are the same as or different from one another and are each hydrogen atom or methyl group; of which compounds of Formula (1) in which $R^1$ to $R^{20}$ are hydrogen atoms are particularly preferred. This is because these compounds have high oxirane oxygen concentrations, have low molecular weights between crosslinking points, and can give cured articles having a higher crosslinking density.

Method for Producing Triepoxy Compound

The triepoxy compound represented by Formula (1) can be produced typically by oxdizing a compound represented by Formula (2) with an oxidizing agent, Formula (2) expressed as follows:

[Chem. 8]

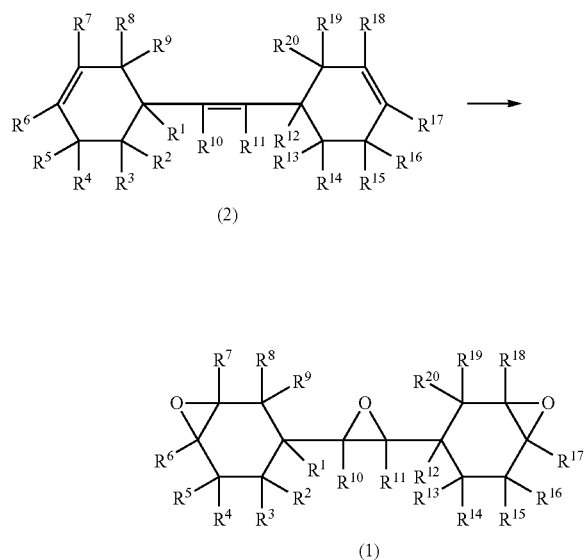

In Formula (2), $R^1$ to $R^{20}$ are the same as or different from one another and each represent hydrogen atom, methyl group, or ethyl group and correspond to $R^1$ to $R^{20}$, respectively, in the triepoxy compound represented by Formula (1).

The oxidizing agent for use in the reaction of oxidizing the compound represented by Formula (2) (hereinafter also referred to as "oxidation reaction") is exemplified by peracids and peroxides. The peracids are exemplified by organic peracids such as performic acid, peracetic acid, trifluoroperacetic acid, perbenzoic acid, meta-chloroperbenzoic acid, and monoperoxyphthalic acid; and inorganic peracids such as permanganic acid. The peroxides are exemplified by hydrogen peroxide, peroxides, hydroperoxides, peroxoacids, and peroxoacid salts. Among them, one or more peracids are preferably employed herein because they can efficiently give the triepoxy compound represented by Formula (1) without using a catalyst.

The oxidizing agent may be used in an amount of typically from about 3.0 to about 8.0 moles, preferably from about 3.1 to about 6.0 moles, and particularly preferably from about 3.2 to about 4.0 moles, per 1 mole of the compound represented by Formula (2). The oxidizing agent, if used in an amount larger than the above-specified range, may cause an economical disadvantage and may readily increase side reactions to adversely affect the yield of the triepoxy compound represented by Formula (1). In contrast, the oxidizing agent, if used in an amount smaller than the above-specified range, may readily cause a monoepoxide and/or a diepoxide to form in a larger amount.

The oxidation reaction is performed in the presence of, or in the absence of, a solvent. The solvent is exemplified by alcohols such as t-butyl alcohol; aliphatic hydrocarbons such as hexane, heptane, and octane; alicyclic hydrocarbons such as cyclohexane; aromatic hydrocarbons such as benzene, toluene, xylenes, and ethylbenzene; halogenated hydrocarbons such as chloroform, methylene chloride, and 1,2-dichloroethane; chain or cyclic ethers such as ethyl ether and tetrahydrofuran; esters such as ethyl acetate; amides such as N,N-dimethylformamide and N,N-dimethylacetamide; nitriles such as acetonitrile, propionitrile, and benzonitrile; and organic acids such as acetic acid. Each of such solvents may be used alone or in combination.

The solvent may be used in an amount of typically from 1 to about 15 times by weight, and preferably from about 2 to about 12 times by weight larger than that of the compound represented by Formula (2).

The reaction may be performed at a temperature of typically from about 0° C. to about 90° C., and preferably from 20° C. to 70° C. for a time of typically from about 1 to about 10 hours, and preferably from 2 to 6 hours. The reaction may be performed under normal atmospheric pressure, under reduced pressure, or under a pressure (under a load). The reaction may be performed in any atmosphere such as an air atmosphere, nitrogen atmosphere, or argon atmosphere, not limited unless adversely affecting the reaction. The reaction may be performed according to any system such as a batch system, semi-batch system, or continuous system.

The oxidation reaction can be terminated by the addition typically of sodium thiosulfate or sodium sulfite.

After the termination of reaction, a reaction product can be separated/purified by a separation process such as filtration, concentration, distillation, extraction, crystallization, recrystallization, or column chromatography, or a separation process as a combination of them.

The compound represented by Formula (2) may be produced typically by a method of subjecting a compound represented by Formula (3) and a compound represented by Formula (3') to a metathesis reaction (particularly, an olefin metathesis reaction). In Formulae (3) and (3'), $R^1$ to $R^{10}$ and $R^{11}$ to $R^{20}$ are independent groups, are the same as or different from one another, and represent hydrogen atom, methyl group, or ethyl group. Formulae (3) and (3') are expressed as follows:

[Chem. 9]

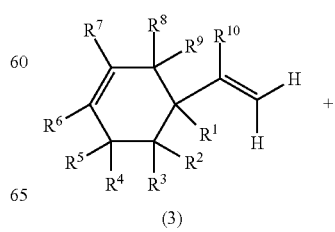

-continued

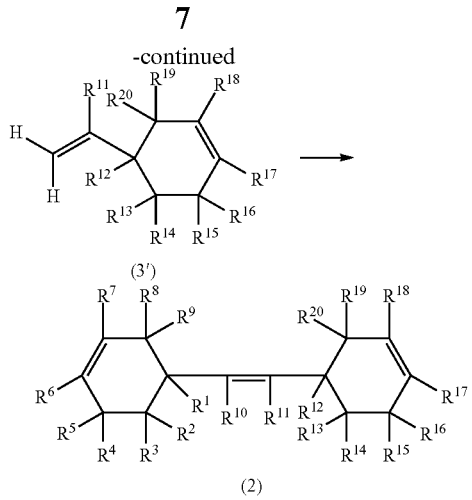

(2)

The metathesis reaction is preferably performed in the presence of a catalyst. The catalyst for use herein is preferably exemplified by ruthenium complex catalysts, tungsten catalysts, molybdenum catalysts, cobalt-molybdenum catalysts, titanium catalysts, and vanadium catalysts; of which ruthenium complex catalysts and cobalt-molybdenum catalysts are particularly preferred.

Of the ruthenium complex catalysts, preferred are ruthenium carbene complexes. The ruthenium carbene complexes are preferably exemplified by commercial products such as Dichloro-(3-phenyl-1H-inden-1-ylidene)bis(tricyclohexylphosphine)ruthenium(II) (trade name "Umicore M1"), Dichloro-(3-phenyl-1H-inden-1-ylidene)bis(isobutylphobane)ruthenium(II) (trade name "Umicore M1$_1$"), [1,3-Bis(2,4,6-trimethylphenyl)-2-imidazolidinylidene]dichloro-(3-phenyl-1H-inden-1-ylidene)(tricyclohexylphosphine)ruthenium(II) (trade name "Umicore M2"), [1,3-Bis(2,4,6-trimethylphenyl)-2-imidazolidinylidene]dichloro-(3-phenyl-1H-inden-1-ylidene)(pyridyl)ruthenium(II) (trade name "Umicore M3$_1$"), [1,3-Bis(2,4,6-trimethylphenyl)-2-imidazolidinylidene]-[2-[[(4-methylphenyl)imino]methyl]-4-nitro-phenolyl]chloro-[3-phenyl-indenylidene]ruthenium (II) (trade name "Umicore M4$_1$"), [1,3-Bis(2,4,6-trimethylphenyl)-2-imidazolidinylidene]-[2-[[(2-methylphenyl)imino]methyl]-phenolyl]chloro-(3-phenyl-indenylidene)ruthenium(II) (trade name "Umicore M4$_2$"), [1,3-bis(2,4,6-trimethylphenyl)-2-imidazolidinylidene]dichloro[2-(1-methylacetoxy)phenyl]methyleneruthenium (II) (trade name "Umicore M51", the above are supplied by Umicore N.V.); bis(tricyclohexylphosphine)benzylidine ruthenium(IV) dichloride or benzylidene-bis(tricyclohexylphosphine)dichlororuthenium (trade name "Grubbs Catalyst, 1st Generation"), (1,3-bis(2,4,6-trimethylphenyl)-2-imidazolidinylidene)dichloro(phenylmethylene)(tricyclohexylphosphine)ruthenium, [1,3-bis-(2,4,6-trimethylphenyl)-2-imidazolidinylidene]dichloro-(phenylmethylene)(tricyclohexylphosphine)ruthenium, or benzylidene[1,3-bis(2,4,6-trimethylphenyl)-2-imidazolidinylidene]dichloro(tricyclohexylphosphine)ruthenium (trade name "Grubbs Catalyst, 2nd Generation"), (dichloro-o-isopropoxyphenylmethylene)(tricyclohexylphosphine)ruthenium(II) (trade name "Hoveyda-Grubbs Catalyst 1st Generation"), (1,3-bis-(2,4,6-trimethylphenyl)-2-imidazolidinylidene)dichloro(o-isopropoxyphenylmethylene)ruthenium (trade name "Hoveyda-Grubbs Catalyst 2nd Generation", the above are supplied by Sigma-Aldrich Co. LLC.); Tricyclohexylphosphine[1,3-bis(2,4,6-trimethylphenyl)imidazol-2-ylidene][2-thienylmethylene]ruthenium(II) dichloride (trade name "catMETium RF 2"), Tricyclohexylphosphine[4,5-dimethyl-1,3-bis(2,4,6-trimethylphenyl)imidazol-2-ylidene][2-thienylmethylene]ruthenium(II) dichloride (trade name "catMETium RF 3"), and Tricyclohexylphosphine[2,4-dihydro-2,4,5-triphenyl-3H-1,2,4-triazol-3-ylidene][2-thienylmethylene]ruthenium(II) dichloride (trade name "catMETium RF 4", the above are supplied by Evonik Industries AG). Each of them may be used alone or in combination.

The ruthenium complex catalyst, when employed in the metathesis reaction, may be used in an amount of typically from about 0.00001 to about 0.01 mole per 1 mole of the compounds represented by Formulae (3) and (3'). The upper limit of the amount of the ruthenium complex catalyst is preferably 0.005 mole, and particularly preferably 0.003 mole. The lower limit of the amount is preferably 0.00002 mole, and particularly preferably 0.00005 mole. The ruthenium complex catalyst, if used in an amount smaller than the above-specified range, may readily give the compound represented by Formula (2) in an insufficient amount. In contrast, the ruthenium complex catalyst, if used in an amount larger than the above-specified range, may cause an economical disadvantage.

The metathesis reaction using the ruthenium complex catalyst may be performed in the presence of, or in the absence of, a solvent. The solvent is exemplified by aliphatic hydrocarbons such as hexane and octane; aromatic hydrocarbons such as toluene and xylenes; alicyclic hydrocarbons such as cyclohexane; halogenated hydrocarbons such as methylene chloride and 1,2-dichloroethane; esters such as ethyl acetate; ethers such as dioxane; and aprotic polar solvents such as N,N-dimethylformamide. Each of them may be used alone or in combination.

The solvent may be used in an amount of typically from about 0 to about 2000 parts by weight, and preferably from 0 to 500 parts by weight, per 100 parts by weight of the total amount of the compounds represented by Formulae (3) and (3').

The metathesis reaction, when employing the ruthenium complex catalyst, may be performed at a temperature suitably selected according typically to the types of reaction components and catalyst. Typically, the reaction may be performed at a temperature of from 10° C. to about 100° C., preferably from about 20° C. to about 80° C., and more preferably from about 30° C. to about 50° C. for a time of typically from about 5 to about 100 hours, and preferably from 12 to 60 hours. The reaction may be performed under normal atmospheric pressure, under reduced pressure, or under a pressure (under a load). The reaction may also be performed in any atmosphere such as a nitrogen atmosphere or argon atmosphere, not limited unless adversely affecting the reaction. The reaction may be performed according to any system such as a batch system, semi-batch system, or continuous system.

Examples of the cobalt-molybdenum catalysts include cobalt oxide-molybdenum oxide/alumina catalysts and other catalysts bearing cobalt oxide and molybdenum oxide on a support. The support is exemplified by alumina, silica, silica-alumina, zirconium oxide, cerium oxide, and titanium oxide. The examples of the cobalt-molybdenum catalysts further include cobalt oxide-molybdenum oxide-potassium/alumina catalysts, cobalt oxide-molybdenum oxide-cesium/alumina catalysts, cobalt oxide-molybdenum oxide-calcium/alumina catalysts, and other catalysts each bearing, in addition to cobalt oxide and molybdenum oxide, an alkali metal and/or an alkaline earth metal on a support. The alkali metal is exemplified by potassium, sodium, and cesium. The alkaline earth metal is exemplified by calcium, strontium, and barium. The support is exemplified by alumina, silica, silica-alumina, zirconium oxide, cerium oxide, and titanium oxide. Each of the catalysts may be used alone or in combination.

A metathesis reaction employing the cobalt-molybdenum catalyst may be performed as a gas phase reaction (e.g., a gas phase flow reaction) or as a liquid phase reaction (e.g., a liquid phase flow reaction or a liquid phase batch reaction). A reaction temperature may be suitably selected according typically to the types of the reaction components and the catalyst and may be typically from 90° C. to 200° C., and preferably from 100° C. to 190° C. The reaction may be performed under normal atmospheric pressure, under reduced pressure, or under a pressure (under a load). The reaction may be performed in any atmosphere such as an air atmosphere, nitrogen atmosphere, or argon atmosphere, not limited unless adversely affecting the reaction. The reaction may be performed according to any system such as a batch system, semi-batch system, or continuous system.

The cobalt-molybdenum catalyst, when employed in a metathesis reaction performed as a liquid phase batch reaction, may be used in an amount of typically from about 1 to about 50 parts by weight per 100 parts by weight of the compounds represented by Formulae (3) and (3'). The upper limit of the amount of the cobalt-molybdenum catalyst is preferably 40 parts by weight, and particularly preferably 30 parts by weight. The lower limit thereof is preferably 3 parts by weight, and particularly preferably 15 parts by weight. The cobalt-molybdenum catalyst, if used in an amount smaller than the above-specified range, may readily give the compound represented by Formula (2) in an insufficient amount. In contrast, the cobalt-molybdenum catalyst, if used in an amount larger than the above-specified range, may cause an economical disadvantage. The reaction may be performed for a time of typically from about 5 to about 100 hours, and preferably from 10 to 60 hours.

The compounds represented by (3) and (3'), when employed in a metathesis reaction performed as a flow reaction using the cobalt-molybdenum catalyst, may be fed in an amount per catalyst unit weight per one hour (weight space velocity: WHSV) of from 0.001 to 100 per hour, preferably from 0.01 to 50 per hour, and more preferably from 0.1 to 20 per hour. The compounds, if fed in an excessively small WHSV, may require a larger reactor, thus being uneconomical. In contrast, the compounds, if fed in an excessively large WHSV, may give the target compound with a lower conversion, and this may increase the cost for separating the product from unreacted materials.

A metathesis reaction using the cobalt-molybdenum catalyst, when performed in a liquid phase, can employ such a solvent as not to adversely affect reaction progress. The solvent is exemplified by aliphatic hydrocarbons such as hexane and octane; aromatic hydrocarbons such as toluene and xylenes; and alicyclic hydrocarbons such as cyclohexane. Each of different solvents may be used alone or in combination.

The solvent may be used in an amount of typically from about 0 to about 1000 parts by weight, and preferably from 0 to 500 parts by weight, per 100 parts by weight of the total amount of the compounds represented by Formulae (3) and (3').

In use of any catalyst, a reaction product after the termination of reaction can be separated/purified according to a separation/purification process such as filtration, concentration, distillation, extraction, crystallization, recrystallization, adsorption, or column chromatography, or a process as a combination of them.

The method for producing a triepoxy compound according to the present invention can synthetically produce a triepoxy compound represented by Formula (1) efficiently.

Curable Composition

A curable composition according to an embodiment of the present invention may contain one or more monomer components (cationically polymerizable monomer components) in a content of typically from about 5 to about 100 percent by weight, and preferably from 10 to 99.5 percent by weight based on the total amount (total amount of non-volatile matter) of the curable composition. The curable composition according to the present invention includes the triepoxy compound represented by Formula (1) as a monomer component. The curable composition may contain the triepoxy compound in a content of typically about 20 percent by weight or more, preferably 25 percent by weight or more, particularly preferably 30 percent by weight or more, most preferably 50 percent by weight or more, and furthermore preferably 70 percent by weight or more, of the total amount of entire monomer components contained in the curable composition. The upper limit of the content of the triepoxy compound represented by Formula (1) is 100 percent by weight. The curable composition, when containing the triepoxy compound represented by Formula (1) in a content within the above-specified range, can form, through polymerization, a cured article that has a high crosslinking density and exhibits excellent heat resistance and toughness. This is because the triepoxy compound provides crosslinking points in a large number per monomeric unit. The curable composition, when containing the triepoxy compound represented by Formula (1) in a content lower than the above-specified range, may have crosslinking points in a smaller number per monomeric unit to cause a lower crosslinking density and may readily give a cured article suffering from inferior heat resistance and toughness.

IN addition to the triepoxy compound represented by Formula (1), the curable composition according to the present invention may further contain, as monomer components, one or more other epoxy compounds copolymerizable with the triepoxy compound represented by Formula (1). Such other epoxy compounds are exemplified by alicyclic epoxy compounds, aromatic glycidyl ether epoxy compounds, and aliphatic polyhydric alcohol polyglycidyl ether epoxy compounds.

The curable composition according to the present invention preferably further contains a curing agent and/or a curing catalyst.

As the curing agent, the cured composition can employ any of known or customary compounds used as epoxy-compound-curing agents. Such curing agents are exemplified by acid anhydrides such as 3- or 4-methyl-1,2,3,6-tetrahydrophthalic anhydride, 3- or 4-methyl-hexahydrophthalic anhydride, methyl-3,6-endomethylene-1,2,3,6-tetrahydrophthalic anhydride, and 5-norbornene-2,3-carboxylic anhydride; amines (e.g., chain aliphatic polyamines such as diethylenetriamine and triethylenetetramine; cyclic aliphatic polyamines such as N-aminomethylpiperazine; and aromatic amines such as m-xylenediamine and m-phenylenediamine); polyamide resins; imidazoles such as 2-methylimidazole; amine-$BF_3$ complex compounds; Broensted acid salts such as aliphatic sulfonium salts, aromatic sulfonium salts, iodonium salts, and phosphonium salts; and polycarboxylic acids such as adipic acid, sebacic acid, terephthalic acid, trimellitic acid, and carboxyl-containing polyesters.

Among them, an acid anhydrides is preferably used as the curing agent in the present invention. This is because such an acid anhydride can give a curable composition having a low viscosity and excellent workability, and this curable composition can give a cured article having excellent heat resistance. The acid anhydride for use herein may be any of commercial products such as those under the trade names of "RIKACID MH-700", "RIKACID MH", "RIKACID HH", "RIKACID TH", "RIKACID MT-500", and "RIKACID HNA-100" (the above are supplied by New Japan Chemical Co., Ltd.); under the trade names of "HN-2200", "HN-2000", "HN-5000", "MHAC-P", and "Himic Anhydride" (the above are supplied by Hitachi Chemical Company, Ltd.); and under the trade name of "Quinhard 200" (supplied by ZEON CORPORATION).

The curing agent may be used in an amount of from about 50 to about 130 percent by weight, and preferably from 60 to 120 percent by weight, relative to the total amount of monomer components contained in the curable composition.

The curing agent is preferably used in combination with a curing accelerator. The curing accelerator is exemplified by phosphorus compounds such as triphenylphosphine, and derivatives of them; amine compounds such as benzyldimethylamine, and derivatives of them; quaternary ammonium compounds such as tetrabutylammonium bromide and tetrabenzylammonium bromide, and derivatives of them; imidazole compounds such as 2-ethyl-4-methyl-imidazole, 2,3-dihydro-1H-pyrrolo[1,2a]benzimidazole, and 1-cyanoethyl-2-methyl-imidazole, and derivatives of them; and 1,8-diazabicyclo[5,4,0]undecene-7 and derivatives thereof. The curing accelerator for use herein can be any of commercial products such as those under trade names of "U-CAT SA-1", "U-CAT SA-102", "U-CAT SA-5003", "U-CAT SA-5002", "U-CAT SA-603", "U-CAT 18X", and "U-CAT SA-506" (the above are supplied by San-Apro Ltd.).

The curing accelerator may be used in an amount of typically from about 0.05 to about 5.0 parts by weight, and preferably from 0.1 to 4.0 parts by weight, per 100 parts by weight of the curing agent.

The curing catalyst is exemplified by polymerization initiators such as photo-induced cationic-polymerization initiators and thermal cationic-polymerization initiators.

The photo-induced cationic-polymerization initiators are exemplified by sulfonium salts such as triallylsulfonium hexafluorophosphate and triarylsulfonium hexafluoroantimonates; iodonium salts such as diaryliodonium hexafluorophosphates, diphenyliodonium hexa fluoroantimonate, bis(dodecylphenyl)iodonium tetrakis(pentafluorophenyl)borate, and [4-(4-methylphenyl-2-methylpropyl)phenyl]iodonium hexafluorophosphate; phosphonium salts such as tetrafluorophosphonium hexafluorophosphate; and Pyridium salts. Such photo-induced cationic-polymerization initiators for use herein are available as commercial products such as those under the trade names of "CYRACURE UVI-6994" and "CYRACURE UV1-6974" (the above are supplied by The Dow Chemical Company); under the trade name of "Photoinitiator PI-2074" (supplied by Rhodia Japan, Ltd.); under the trade name of "IRGACURE 250" (supplied by Ciba Japan K.K.); and under the trade names of "CPI-100P" and "CPI-101A" (the above are supplied by San-Apro Ltd.).

The thermal cationic-polymerization initiators are exemplified by aryl diazonium salts, aryl iodonium salts, aryl sulfonium salts, and arene-ion complexes. Such thermal cationic-polymerization initiators for use herein are available as commercial products such as those under the trade names of "PP-33", "CP-66", and "CP-77" (the above are supplied by ADEKA CORPORATION); under the trade name of "FC-509" (supplied by 3M Company); under the trade name of "UVE1014" (supplied by General Electric Company); under the trade names of "San-Aid SI-60L", "San-Aid SI-80L", "San-Aid SI-100L", and "San-Aid SI-110L" (the above are supplied by SANSHIN CHEMICAL INDUSTRY CO., LTD.); and under the trade name of "CG-24-61" (supplied by Ciba Japan K.K.).

The curing catalyst may be used in an amount of typically from about 0.1 to about 10.0 percent by weight, and preferably from about 0.3 to about 3.0 percent by weight, relative to the total amount of monomer components contained in the curable composition.

Where necessary, the curable composition according to the present invention may further contain one or more other additives within ranges not adversely affecting advantageous effects of the present invention. Such other additives are exemplified by organosiloxane compounds, metal oxide particles, rubber particles, silicone- or fluorine-containing antifoaming agents, silane coupling agents, fillers, plasticizers, leveling agents, antistatic agents, releasing agents, flame retardants, colorants, antioxidants, ultraviolet absorbers, ion adsorbents, pigments, and solvents. These additives may be incorporated in an amount of typically from about 5 percent by weight or less based on the total amount (total amount of non-volatile matter) of the curable composition.

The curable composition according to the present invention may be prepared typically by formulating a triepoxy compound represented by Formula (1), and, according to necessity, one or more other copolymerizable monomer components, a curing agent and a curing accelerator, or a curing catalyst, other additives, and other optional components; and stirring and mixing them while debubbling in a vacuum according to necessity. The stirring/mixing may be performed at a temperature of typically from about 10° C. to about 60° C. The stirring/mixing can employ a known device such as a planetary centrifugal mixer, single-screw or multi-screw extruder, planetary mixer, kneader, or dissolver.

The curable composition prepared by the above method may be molded or shaped according to a known or customary forming process; and then subjected typically to a heating treatment to accelerate a polymerization reaction to thereby give a cured article. The heating may be performed at a temperature of typically from about 50° C. to about 200° C., and preferably from 55° C. to 150° C. for a time of typically from about 0.5 to about 12 hours, and preferably from 1 to 10 hours. A heating device for use herein is exemplified by an oven. The resulting article after the heating treatment may further be subjected to postbaking. The postbaking may be performed by heating the article at a temperature of typically from about 50° C. to about 200° C., and preferably from 60° C. to 180° C., for a time of from about 0.5 to about 12 hours, and preferably from 1 to 10 hours.

The polymerization reaction may be performed under normal atmospheric pressure, under reduced pressure, or under a pressure (under a load). The reaction may be performed in any atmosphere such as an air atmosphere, nitrogen atmosphere, or argon atmosphere, not limited unless adversely affecting the reaction.

The resulting cured article according to the present invention thus obtained has excellent heat resistance and has such a temperature as to give a storage elastic modulus (E') of $10^9$ Pa or less of 240° C. or higher, preferably 250° C. or higher, and particularly preferably from 260° C. to 330° C., where the storage elastic modulus is determined by a dynamic viscoelastic measurement. The cured article has a peak top temperature (=inflection-point temperature: corresponding to glass transition temperature) of loss tangent (tan $\delta$=E''/E') of typically 260° C. or higher, preferably 270° C. or higher, and particularly preferably from 280° C. to 350° C.

The cured article according to the present invention can exhibit excellent dimensional stability even at elevated temperatures and has a coefficient of linear expansion of typically about 65 ppm/° C. or less, preferably 60 ppm/° C. or less, particularly preferably 50 ppm/° C. or less, and most preferably 45 ppm/° C. or less.

The curable composition according to the present invention can form a cured article having excellent heat resistance and toughness as described above and is advantageously used typically as machine part materials, electric/electronic component materials, automotive part materials, civil engineering and construction materials, molding materials, coating materials, fiber reinforced plastics (FRPs; such as glass fiber reinforced plastics (GFRPs) and carbon fiber reinforced plastics (CFRPs)) materials, and plastic forming materials.

In addition, the cured article according to the present invention has such reflow-heat resistance as to be applicable to lead-free solder mounting. This enables an article such as a semiconductor device encapsulated with the curable composition according to the present invention to be directly mounted onto a substrate in a mounting process through the same solder reflow process as with surface mounting of other electronic components. This in turn enables extremely efficient production of a product.

EXAMPLES

The present invention will be illustrated in further detail with reference to several examples below. It should be noted, however, that these examples are by no means intended to limit the scope of the invention.

Preparation Example 1

Catalyst Preparation

Fifty (50) grams of a cobalt oxide-molybdenum oxide/alumina (supplied by Strem Chemicals, Inc.) was immersed in 97 g of an aqueous solution containing 3.9 g of potassium nitrate, dried at 60° C., fired at 550° C. in the air, and yielded a cobalt oxide-molybdenum oxide-potassium/alumina catalyst (Catalyst (1)).

Example 1

In a nitrogen atmosphere, 0.08 g (corresponding to 0.0001 mole per 1 mole of 4-vinyl-1-cyclohexene) of [1,3-Bis(2,4,6-trimethylphenyl)-2-imidazolidinylidene]dichloro-(3-phenyl-1H-inden-1-ylidene)(tricyclohexylphosphine)ruthenium (II) (trade name "Umicore M2", supplied by Umicore N.V.) was dissolved in 90.0 g of toluene ("Toluene, Super Dehydrated", supplied by Wako Pure Chemical Industries, Ltd.), and the solution was charged into a 300-mL three-necked flask.

While blowing nitrogen into a gas phase, 89.5 g of 4-vinyl-1-cyclohexene was charged using a syringe, followed by stirring at 40° C. for 24 hours. The reaction mixture was concentrated to give a concentrated residue, the residue was purified through simple distillation under reduced pressure (0.9 kPa), and yielded 37.1 g of Compound (II) represented by a formula below. Compound (II) was obtained as a fraction at 125° C. to 126° C. in a yield of 47.4% on the basis of 4-vinyl-1-cyclohexene.

It was verified through $^1$H-NMR that a proton peak at δ of 5.1-4.9 assigned to terminal olefin of 4-vinyl-1-cyclohexene disappeared.

$^1$H-NMR (500 MHz, CDCl$_3$, relative to TMS) δ 5.7-5.6 (m, 4H), 5.5-5.2 (m, 4H), 2.3-1.3 (m, 14H)

[Chem. 10]

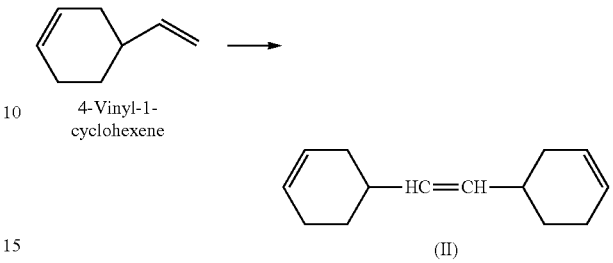

Example 2

Under atmospheric pressure, 4-vinyl-1-cyclohexene was passed continuously through 3.6 g of Catalyst (1) at a rate of 5.0 g per hour. Catalyt (1) had been obtained in Preparation Example 1 and was held herein at 135° C. In a time period from 2 hours to 5 hours after the initiation of passage, 14.4 g of a liquid containing Compound (II) represented by the formula was obtained. This process was performed at a WHSV of 1.4 per hour. Quantitative determination of 4-vinyl-1-cyclohexene and Compound (II) was performed according to a gas chromatography internal standard method to find that Compound (II) was obtained in a yield of 34.9% on the basis of 4-vinyl-1-cyclohexene with a conversion from 4-vinyl-1-cyclohexene of 37.8%.

Example 3

A liquid (15.3 g) containing Compound (II) represented by the formula was obtained by the procedure of Example 2, except for passing 4-vinyl-1-cyclohexene continuously through the catalyst at a rate of 5.4 g per hour and at a temperature of 123° C., lower than the boiling point thereof. This process was performed at a WHSV of 1.5 per hour. Quantitative determination of 4-vinyl-1-cyclohexene and Compound (II) was performed according to the gas chromatography internal standard method to find that Compound (II) was obtained in a yield of 30.1% on the basis of 4-vinyl-1-cyclohexene with a conversion from 4-vinyl-1-cyclohexene of 33.2%.

Example 4

In a nitrogen atmosphere, 2.4 g (24 parts by weight per 100 parts by weight of 4-vinyl-1-cyclohexene) of Catalyst (1) obtained in Preparation Example 1 and 10 g of 4-vinyl-1-cyclohexene were stirred with each other at 120° C. and normal atmospheric pressure for 15 hours and yielded 8.3 g of a liquid containing Compound (II) represented by the formula. Quantitative determination of 4-vinyl-1-cyclohexene and Compound (II) was performed according to the gas chromatography internal standard method to find that Compound (II) was obtained in a yield of 66.5% on the basis of 4-vinyl-1-cyclohexene with a conversion from 4-vinyl-1-cyclohexene of 80.7%.

Example 5

Synthesis of 2,3-Bis(3,4-epoxycyclohexyl)oxirane: Compound (I)

In 150 g of ethyl acetate was dissolved 15 g (0.08 mol) of Compound (II) represented by a formula below. To this was added 65.5 g (0.26 mol) of meta-chloroperbenzoic acid at 30° C. over one hour, followed by stirring at 30° C. for 2 hours. The resulting reaction mixture was combined with 379 g of a 10 percent by weight aqueous sodium thiosulfate solution, stirred for 30 minutes, further combined with 150 g of toluene, and separated. The aqueous layer was extracted again with 150 g of toluene.

The obtained organic layers were combined, washed with two portions of 384 g of a 7 percent by weight aqueous sodium hydrogencarbonate solution and with two portions of 300 g of water, and the resulting organic layer was concentrated.

The concentrated residue was purified through silica gel column chromatography and yielded 12.1 g of Compound (I) represented by a formula below as a colorless, transparent, viscous liquid. Compound (I) was obtained in a yield of 64% on the basis of Compound (II).

It was verified through $^1$H-NMR that a peak at δ of 5.8 to 5.2 ppm assigned to the double bond of Compound (II) disappeared; and that proton peaks at δ of 3.3 to 3.1 ppm and 2.7 to 2.4 ppm assigned to epoxy group were formed.

1H-NMR (500 MHz, CDCl$_3$, relative to TMS) δ 3.28-3.07 (m, 8H), 2.72-2.39 (m, 2H), 2.27-1.01 (m, 14H)

An oxirane oxygen concentration was determined by titration using a solution of hydrogen bromide in acetic acid and found to be 19.98 percent by weight, which is 98% of a theoretical value (20.31 percent by weight). The formula is expressed as follows:

[Chem. 11]

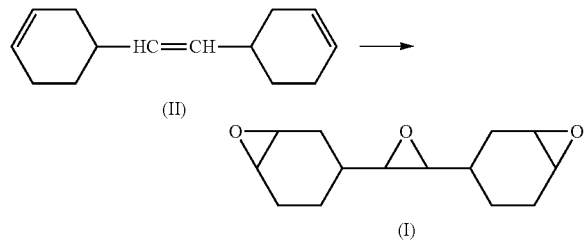

Example 6

Curable Composition (1) was obtained by combining 100 parts by weight of Compound (I) obtained in Example 5 with 0.6 part by weight of an arylsulfonium salt (trade name "San-Aid SI-100L", supplied by SANSHIN CHEMICAL INDUSTRY CO., LTD., hereinafter also referred to as "SI-100L") as a thermal cationic-polymerization initiator.

Comparative Example 1

Curable Composition (2) was obtained by the procedure of Example 6, except for using 100 parts by weight of 3,4-epoxycyclohexylmethyl (3,4-epoxy)cyclohexanecarboxylate (trade name "CEL 2021P", supplied by Daicel Corporation; hereinafter also referred to as "CEL 2021P") represented by a formula below, instead of Compound (I). CEL 2021P had a theoretical oxirane oxygen concentration of 12.68 percent by weight as determined from its structural formula. The formula is expressed as follows:

[Chem. 12]

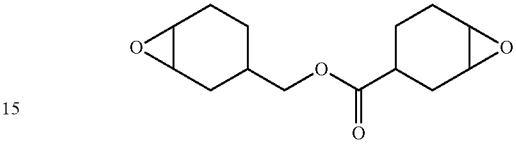

Curable Compositions (1) and (2) obtained in Example 6 and Comparative Example 1 were respectively cast into a glass tube having an inner diameter of 6 mm, cured at 65° C. for 2.5 hours, further cured at 150° C. for 1.5 hours, and yielded transparent Cured Articles (1) and (2).

The obtained Cured Articles (1) and (2) were subjected to measurements of glass transition point and coefficient of linear expansion (ppm/° C.: as a value at a temperature equal to or lower than the glass transition point) using a thermomechanical analyzer (trade name "TMA/SS7100", supplied by Seiko Instruments Inc.) under conditions as follows:

Measurement Conditions

Temperature Range: 30° C. to 300° C.
Rate of Temperature Rise: 5° C./min.

Curable Compositions (1) and (2) obtained in Example 6 and Comparative Example 1 were respectively cured at 65° C. for 2.5 hours, further cured at 150° C. for 1.5 hours, and yielded thin sheets having a thickness of from about 1 to about 2 mm. These were cut into strips having a length of about 40 mm and a width of from about 3 to about 4 mm and yielded Cured Articles (3) and (4).

The obtained Cured Articles (3) and (4) were each subjected to measurements of storage elastic modulus (E') and loss elastic modulus (E") using a solids viscoelastic analyzer (trade name "RSA-III", supplied by TA Instruments, Inc.) in a nitrogen atmosphere with temperature rise from 10° C. up to 300° C. at a rate of 5° C./min, in a tensile mode at a forced frequency of 10 Hz. Based on the resulting data, a temperature (° C.) at which the storage elastic modulus (E') be 10$^9$ Pa; and a peak top temperature (° C.) of the loss tangent (tan δ=E"/E') were determined. Compound (I) had neither a distinct inflection point nor a distinct peak top, and the temperature (° C.) at which the storage elastic modulus (E') be 10$^9$ Pa was employed as an index for heat resistance.

TABLE 1

| | | | Example 6 | Comparative Example 1 |
|---|---|---|---|---|
| Resin composition | Epoxy compound | Compound (I) | 100 | — |
| | | CEL2021P | — | 100 |
| | Thermal cationic-polymerization initiator | SI-100L | 0.6 | 0.6 |
| Evaluation | Temperature (° C.) at which storage elastic modulus be 10$^9$ Pa | | >300 *[1] | 204 |
| | Peak top temperature (° C.) of tan δ | | *[2] | 243 |
| | Glass transition point (° C.) | | 227.2 | 146.4 |
| | Coefficient of linear expansion (ppm/° C.) | | 43.2 | 67.1 |

*[1] The sample had a storage elastic modulus of 1.3 × 10$^9$ Pa at 300° C.
*[2] No distinct peak top was observed.

Table 1 demonstrated that triepoxy compounds according to the present invention could form cured articles having heat resistance superior to that of cured articles of diepoxy compounds having two epoxy groups per molecule; and that the triepoxy compounds could form cured articles less suffering from dimensional change by heating, having excellent dimensional stability, and having excellent adhesion to various substrates.

INDUSTRIAL APPLICABILITY

The novel triepoxy compounds represented by Formula (1) according to embodiments of the present invention can form, through polymerization, cured articles having more excellent heat resistance and are useful as machine part materials, electric/electronic component materials, automotive part materials, civil engineering and construction materials, molding materials, coating materials, fiber reinforced plastics (FRPs; such as glass fiber reinforced plastics (GFRPs) and carbon fiber reinforced plastics (CFRPs)) materials, and plastic forming materials.

The invention claimed is:

1. A triepoxy compound represented by Formula (1) expressed as follows:

[Chem. 1]

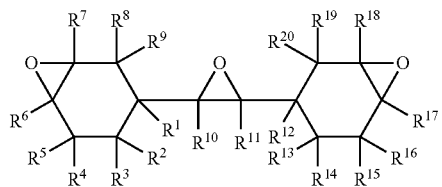

(1)

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are the same as or different from one another and each represent hydrogen atom, methyl group, or ethyl group.

2. A method for producing a triepoxy compound, the method comprising the step of oxidizing a compound represented by Formula (2) with an oxidizing agent to give a triepoxy compound represented by Formula (1), Formula (2) expressed as follows:

[Chem. 2]

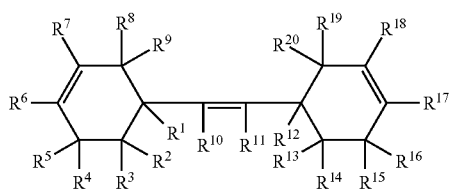

(2)

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are the same as or different from one another and each represent hydrogen atom, methyl group, or ethyl group; and Formula (1) expressed as follows:

[Chem. 3]

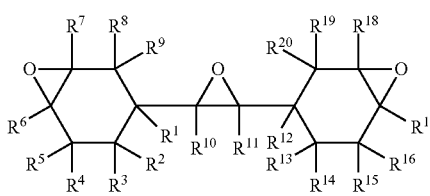

(1)

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ are as defined above.

3. The method for producing a triepoxy compound according to claim 2, wherein the oxidizing agent comprises a peracid.

4. The method for producing a triepoxy compound according to one of claims 2 and 3, further comprising the step of:

subjecting a compound represented by Formula (3) and a compound represented by Formula (3') to a metathesis reaction in the presence of a catalyst to give a compound represented by Formula (2); and using the prepared compound represented by Formula (2) in the step of oxidizing, Formula (3) expressed as follows:

[Chem. 4]

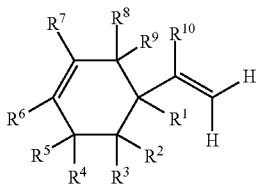

(3)

where $R^1$, $R^2$, $R^3$, $R^4$, $R^5$, $R^6$, $R^7$, $R^8$, $R^9$, and $R^{10}$ are the same as or different from one another and each represent hydrogen atom, methyl group, or ethyl group;

Formula (3') expressed as follows:

[Chem. 5]

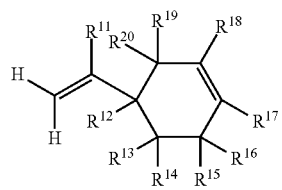

(3')

where $R^{11}$, $R^{12}$, $R^{13}$, $R^{14}$, $R^{15}$, $R^{16}$, $R^{17}$, $R^{18}$, $R^{19}$, and $R^{20}$ are the same as or different from one another and each represent hydrogen atom, methyl group, or ethyl group; and Formula (2) expressed as follows:

[Chem. 6]

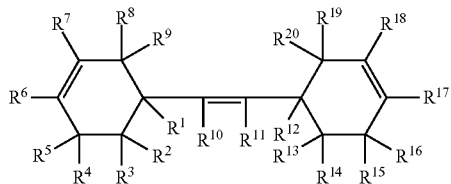
(2)

where $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}$, and $R^{20}$ are as defined above.

5. The method for producing a triepoxy compound according to claim 4, wherein the catalyst comprises a ruthenium complex catalyst or a cobalt-molybdenum catalyst.

6. A curable composition comprising a triepoxy compound represented by Formula (I) expressed as follows:

[Chem. 7]

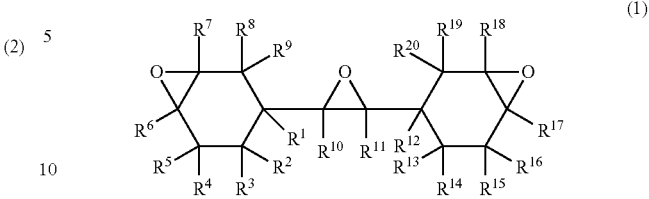
(1)

where $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}$, and $R^{20}$ are the same as or different from one another and each represent hydrogen atom, methyl group, or ethyl group.

7. A cured article obtained by curing the curable composition of claim 6.

* * * * *